(12) United States Patent
Goredema et al.

(10) Patent No.: US 8,029,861 B2
(45) Date of Patent: Oct. 4, 2011

(54) INK CARRIERS CONTAINING LOW VISCOSITY FUNCTIONALIZED WAXES, PHASE CHANGE INKS INCLUDING SAME, AND METHODS FOR MAKING SAME

(75) Inventors: Adela Goredema, Mississauga (CA); Caroline M. Turek, Mississauga (CA); Christopher A. Wagner, Toronto (CA); C. Geoffrey Allen, Waterdown (CA)

(73) Assignee: Xerox Corporation, Norwalk, CT (US)

( * ) Notice: Subject to any disclaimer, the term of this patent is extended or adjusted under 35 U.S.C. 154(b) by 583 days.

(21) Appl. No.: 12/236,029

(22) Filed: Sep. 23, 2008

(65) Prior Publication Data
US 2010/0075038 A1 Mar. 25, 2010

(51) Int. Cl.
*B05D 5/00* (2006.01)
*C09D 11/02* (2006.01)
*C07C 69/02* (2006.01)

(52) U.S. Cl. .............. 427/283; 106/31.13; 106/31.27; 106/31.29; 106/31.61; 427/256; 554/227

(58) Field of Classification Search .............. 427/283, 427/256; 554/227; 106/31.13, 31.27, 31.29, 106/31.61
See application file for complete search history.

(56) References Cited

U.S. PATENT DOCUMENTS

| 3,172,892 A | 3/1965 | Le Suer et al. ............... 548/546 |
|---|---|---|
| 3,202,678 A | 8/1965 | Stuart et al. .................. 548/546 |
| 3,219,666 A | 11/1965 | Norman et al. ............... 544/383 |
| 3,280,034 A | 10/1966 | Anzenberger et al. ........ 508/285 |
| 3,361,673 A | 1/1968 | Stuart et al. .................. 508/293 |
| 3,381,022 A | 4/1968 | Le Suer et al. ............... 554/223 |
| 3,442,808 A | 5/1969 | Traise et al. .................. 508/192 |
| 3,653,932 A | 4/1972 | Berry et al. .................. 106/31.29 |
| 3,912,764 A | 10/1975 | Palmer, Jr. ................... 549/255 |
| 3,996,059 A | 12/1976 | Stansfield et al. ............ 106/413 |
| 4,234,435 A | 11/1980 | Meinhardt et al. ............ 508/192 |
| 4,251,824 A | 2/1981 | Hara et al. .................... 347/57 |
| 4,390,369 A | 6/1983 | Merritt et al. ................ 106/31.3 |
| 4,410,899 A | 10/1983 | Haruta et al. ................. 347/56 |
| 4,412,224 A | 10/1983 | Sugitani ....................... 347/65 |
| 4,484,948 A | 11/1984 | Merritt et al. ................ 106/31.3 |
| 4,490,731 A | 12/1984 | Vaught ......................... 347/88 |
| 4,532,530 A | 7/1985 | Hawkins ...................... 347/62 |
| 4,601,777 A | 7/1986 | Hawkins et al. .............. 216/27 |
| 4,684,956 A | 8/1987 | Ball ............................. 347/88 |
| 4,830,671 A | 5/1989 | Frihart et al. ................ 106/31.29 |
| 4,851,045 A | 7/1989 | Taniguchi .................... 106/31.31 |
| 4,889,560 A | 12/1989 | Jaeger et al. ................. 106/31.29 |
| 4,889,761 A | 12/1989 | Titterington et al. ......... 428/32.1 |
| 5,006,170 A | 4/1991 | Schwarz et al. .............. 106/31.3 |
| 5,151,120 A | 9/1992 | You et al. ..................... 106/31.29 |
| 5,194,638 A | 3/1993 | Frihart et al. ................. 554/47 |
| 5,221,335 A | 6/1993 | Williams et al. .............. 524/560 |
| 5,231,135 A | 7/1993 | Machell et al. ............... 525/123 |
| 5,286,799 A | 2/1994 | Harrison et al. .............. 525/285 |
| 5,319,030 A | 6/1994 | Harrison et al. .............. 525/285 |
| 5,372,852 A | 12/1994 | Titterington et al. .......... 427/288 |
| 5,496,879 A | 3/1996 | Griebel et al. ................. 524/320 |
| 5,597,856 A | 1/1997 | Yu et al. ......................... 524/227 |
| 5,621,022 A | 4/1997 | Jaeger et al. ................... 523/161 |
| 5,750,604 A | 5/1998 | Banning et al. ................ 524/187 |
| 5,780,528 A | 7/1998 | Titterington et al. .......... 523/161 |
| 5,782,966 A | 7/1998 | Bui et al. ...................... 106/31.43 |
| 5,783,658 A | 7/1998 | Banning et al. ................ 101/491 |
| 5,827,918 A | 10/1998 | Titterington et al. .......... 524/590 |
| 5,830,942 A | 11/1998 | King et al. ..................... 524/590 |
| 5,854,359 A | 12/1998 | Yang ............................. 525/444 |
| 5,919,839 A | 7/1999 | Titterington et al. .......... 523/161 |
| 6,039,998 A | 3/2000 | Sekula et al. .................. 426/605 |
| 6,174,937 B1 | 1/2001 | Banning et al. ................ 523/160 |
| 6,255,432 B1 | 7/2001 | Evans et al. .................... 528/49 |
| 6,309,453 B1 | 10/2001 | Banning et al. ............. 106/31.29 |
| 6,472,523 B1 | 10/2002 | Banning et al. ................ 540/128 |
| 6,476,219 B1 | 11/2002 | Duff et al. ...................... 540/128 |
| 6,544,578 B2 | 4/2003 | Sekula et al. .................. 426/605 |
| 6,547,380 B2 | 4/2003 | Smith et al. ..................... 347/96 |
| 6,576,747 B1 | 6/2003 | Carlini et al. .................. 534/649 |
| 6,576,748 B1 | 6/2003 | Carlini et al. .................. 534/649 |
| 6,590,082 B1 | 7/2003 | Banning et al. ................ 534/649 |
| 6,646,111 B1 | 11/2003 | Carlini et al. .................. 534/649 |
| 6,663,703 B1 | 12/2003 | Wu et al. ..................... 106/31.29 |
| 6,673,139 B1 | 1/2004 | Wu et al. ..................... 106/31.29 |
| 6,696,552 B2 | 2/2004 | Mayo et al. .................... 534/649 |
| 6,702,884 B2 | 3/2004 | Brown ......................... 106/31.61 |
| 6,713,614 B2 | 3/2004 | Carlini et al. .................. 534/649 |
| 6,726,755 B2 | 4/2004 | Titterington et al. ...... 106/31.29 |
| 6,755,902 B2 | 6/2004 | Banning et al. ............. 106/31.29 |
| 6,841,590 B2 | 1/2005 | Modi et al. ..................... 523/160 |
| 6,858,070 B1 | 2/2005 | Wong et al. ................. 106/31.61 |
| 6,860,930 B2 | 3/2005 | Wu et al. ..................... 106/31.29 |
| 6,906,118 B2 | 6/2005 | Goodbrand et al. ........... 523/160 |
| 6,958,406 B2 | 10/2005 | Banning et al. ................ 552/243 |

(Continued)

FOREIGN PATENT DOCUMENTS

EP 0187352 7/1986

(Continued)

OTHER PUBLICATIONS

European Search Report, Application No. 09169793.8-2102, dated Jan. 20, 2010, 5 pages.
Canadian Patent Office Communication dated May 12, 2011, for related Canadian Patent application No. 2,678,869, 3 pages.

*Primary Examiner* — Timothy J. Kugel
(74) *Attorney, Agent, or Firm* — Marylou J. Lavoie, Esq. LLC

(57) ABSTRACT

A phase change ink including a colorant and a carrier including a tri-ester of the formula

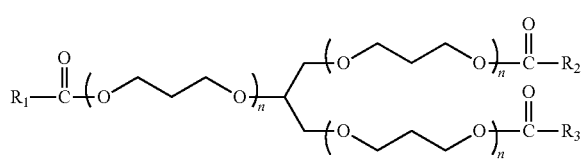

wherein $R_1$, $R_2$ and $R_3$, and n are as defined herein.

25 Claims, No Drawings

U.S. PATENT DOCUMENTS

| | | |
|---|---|---|
| 7,053,227 B2 | 5/2006 | Jaeger et al. .................. 552/247 |
| 7,381,254 B2 | 6/2008 | Wu et al. .................... 106/31.29 |
| 2007/0119340 A1 | 5/2007 | Breton et al. ............. 106/31.43 |
| 2007/0120927 A1 | 5/2007 | Snyder et al. .................. 347/100 |
| 2008/0021147 A1 | 1/2008 | Lin ............................... 524/493 |
| 2008/0098927 A1 | 5/2008 | Allen et al. .................. 106/31.6 |

FOREIGN PATENT DOCUMENTS

| | | |
|---|---|---|
| EP | 0206286 | 12/1986 |
| EP | 0 353 928 A2 | 2/1990 |
| EP | 0 726 030 A2 | 8/1996 |
| EP | 0776963 | 6/1997 |
| EP | 0759422 | 10/1999 |
| EP | 1 067 157 A1 | 1/2001 |
| EP | 1 085 063 A2 | 3/2001 |
| GB | 2238792 | 6/1991 |
| GB | 2290793 | 1/1993 |
| GB | 2294939 | 5/1996 |
| GB | 2305670 | 4/1997 |
| GB | 2305928 | 4/1997 |
| WO | WO 94/04619 | 3/1994 |
| WO | WO 94/14902 | 7/1994 |
| WO | WO 95/04760 | 2/1995 |
| WO | WO 96/14364 | 5/1996 |
| WO | WO 97/12003 | 4/1997 |
| WO | WO 97/13816 | 4/1997 |
| WO | WO 97/33943 | 9/1997 |

INK CARRIERS CONTAINING LOW VISCOSITY FUNCTIONALIZED WAXES, PHASE CHANGE INKS INCLUDING SAME, AND METHODS FOR MAKING SAME

BACKGROUND

Disclosed herein are low viscosity tri-esters, ink carriers, phase change ink compositions including the tri-esters, and methods for making same. More specifically, disclosed herein are ink carriers and phase change inks including low viscosity functionalized waxes, which can be used in direct and indirect printing processes. In embodiments, the ink carriers comprise a low viscosity tri-ester derived from a renewable resource.

Another embodiment is directed to a method which comprises (a) incorporating into an ink jet printing apparatus the above-described phase change ink composition; (b) melting the ink; (c) causing droplets of the melted ink to be ejected in an imagewise pattern onto the surface of the recording substrate, either directly or via an intermediate heated transfer belt or drum, where the droplets quickly solidify to form a predetermined pattern of solidified ink drops.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes.

The colorants can also include pigments, as disclosed in, for example, U.S. Pat. No. 5,221,335, the disclosure of which is totally incorporated herein by reference.

Phase change inks have also been used for applications such as postal marking, industrial marking, and labeling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. No. 3,653,932, U.S. Pat. No. 4,390,369, U.S. Pat. No. 4,484,948, U.S. Pat. No. 4,684,956, U.S. Pat. No. 4,851,045, U.S. Pat. No. 4,889,560, U.S. Pat. No. 5,006,170, U.S. Pat. No. 5,151,120, U.S. Pat. No. 5,372,852, U.S. Pat. No. 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

Ink jetting devices are known in the art, and thus extensive description of such devices is not required herein. As described in U.S. Pat. No. 6,547,380, incorporated herein by reference in its entirety, ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

In a typical design of a piezoelectric ink jet device utilizing phase change inks printing directly on a substrate or on an intermediate transfer member, such as the one described in U.S. Pat. No. 5,372,852, incorporated herein by reference in its entirety, the image is applied by jetting appropriately colored inks during four to eighteen rotations (incremental movements) of a substrate (an image receiving member or intermediate transfer member) with respect to the ink jetting head, i.e., there is a small translation of the printhead with respect to the substrate in between each rotation. This approach simplifies the printhead design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

Thermal ink jet processes are well known and are described, for example, in U.S. Pat. Nos. 4,601,777, 4,251,824, 4,410,899, 4,412,224 and 4,532,530, the disclosures of each of which are hereby incorporated herein in their entireties.

Ink jet printing processes may employ inks that are solid at room temperature and liquid at elevated temperatures. Such inks may be referred to as hot melt inks or phase change inks. For example, U.S. Pat. No. 4,490,731, which is hereby incorporated by reference herein in its entirety, discloses an apparatus for dispensing solid ink for printing on a substrate such as paper. In thermal ink jet printing processes employing hot melt inks, the solid ink is melted by the heater in the printing apparatus and utilized (i.e., jetted) as a liquid in a manner similar to that of conventional thermal ink jet printing. Upon contact with the printing substrate, the molten ink solidifies rapidly, enabling the colorant to substantially remain on the surface of the substrate instead of being carried into the substrate (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of nonprinting without the danger of nozzle clogging, even without capping the nozzles.

Examples of the phase change inks herein are inks that include an ink vehicle that is solid at temperatures of about 23° C. to about 27° C., for example room temperature, and specifically are solid at temperatures below about 60° C. However, the inks change phase upon heating, and are in a molten state at jetting temperatures. Thus, the inks have a viscosity of from about 1 to about 20 centipoise (cp), for example from about 5 to about 15 cp or from about 8 to about 12 cp, at an elevated temperature suitable for ink jet printing, for example temperatures of from about 60° C. to about 150° C.

In embodiments, the inks herein may be low energy inks. Low energy inks are solid at a temperature below about 40° C. and have a viscosity of from about 1 to about 20 centipoise such as from about 5 to about 15 centipoise, for example from about 8 to about 12 cp, at a jetting temperature of from about 60° C. to about 100° C. such as about 80° C. to about 100° C., for example from about 90° C. to about 120° C.

U.S. Patent Publication 20070120927 of Trevor J. Snyder, et al., U.S. Ser. No. 11/290,265, published May 31, 2007, entitled "Phase Change Inks," which is hereby incorporated by reference herein in its entirety, describes a phase change ink composition comprising an ink carrier and a colorant, said ink being suitable for use in an indirect printing process wherein the ink is jetted from a printhead onto a heated intermediate transfer member and subsequently transferred from the intermediate transfer member to a final recording substrate, wherein: (a) the ink can be jetted from the printhead onto the intermediate transfer member when the ink is maintained at a temperature of about 125° C. or lower; (b) the ink can be jetted without purging from a printer maintained at a standby temperature of about 100° C. or lower; and (c) the ink has a cohesive failure temperature of at least about 56° C.

U.S. Pat. No. 7,381,254 of Bo Wu, et al., entitled "Phase Change Inks," which is hereby incorporated by reference herein in its entirety, describes a phase change ink comprising (a) a colorant and (b) a phase change ink carrier, said carrier comprising (i) a branched triamides and (ii) a polyethylene wax having an average peak molecular weight of from about 350 to about 730 and a polydispersity of from about 1.0001 to about 1.500.

A need remains for improved phase change inks, and more specifically, phase change inks suitable for production, transactions printing, and packaging which have improved print quality characteristics and are therefore more robust inks. A need remains for a phase change ink having improved abrasion resistance and improved adhesion to paper. There is also a need to decrease the cost of solid ink while enhancing performance.

U.S. Patent Publication Number 20080098927 of C. Geoffrey Allen et al., U.S. Ser. No. 11/553,294, Published May 1, 2008, entitled "Pigmented Phase Change Inks," which is hereby incorporated by reference herein in its entirety, describes in embodiments inks that include an ink vehicle, pigment particles, and a dispersant that stabilizes the pigment particles, for example by comprising first functional groups that anchor the dispersant to the pigment particles and second functional groups that are compatible with the ink vehicle.

U.S. Pat. No. 6,309,453 to Jeffrey H. Banning et al. entitled "Colorless Compounds, Solid Inks, and Printing Methods," which is hereby incorporated by reference herein in its entirety, describes synthesis of urethanes from glycerol propoxylate and discloses colorless compounds having a central core and at least two arms extending from the core. The core can comprises one or more atoms. The at least two arms have the formula as described therein. In other aspects, U.S. Pat. No. 6,309,453 encompasses phase change inks incorporating the described colorless compound as a toughening agent, and methods of printing with such phase change inks. U.S. Pat. No. 6,309,453 further discloses a solid ink comprising a colorant and a colorless compound of the formula as described therein.

U.S. Pat. No. 6,039,998 to Bernard Charles Sekula et al. entitled "Freezable Low-Calorie spoonable Dressing and Method for Their Production," which is hereby incorporated by reference herein in its entirety, describes esters made from $C_{10}$-$C_{24}$ fatty acids and their use in making spoonable dressings. U.S. Pat. No. 6,039,998 discloses, in embodiments, a reduced calorie spoonable dressing that exhibits freeze-thaw stability. The dressing is made by replacing some or all of the blending salad oil with a fatty acid-esterified propoxylated glycerin composition having from about 3 to about 16 oxypropylene units per unit of glycerin.

European Patent Number EP 0 759 422 B1 entitled "Direct Esterification of Propoxylated Glycerin," Inventor "Michael R. Coatesville, Proprietor, ARCO Chemical Technology, L. P., which is hereby incorporated by reference herein in its entirety, describes a method for making $C_{10}$ to $C_{23}$ esters for the food industry. EP 0 759 422 discloses in embodiments therein a process for producing a fatty acid-esterified propoxylated glycerin comprising: (a) introducing a propoxylated glycerin and a molar excess of fatty acid into a reaction zone to form a reaction mixture; (b) beginning at an initial temperature of from 20° C. to 80° C. and an initial pressure of from 89.6 to 1103 Kpa (13 to 16 psia), simultaneously reducing the pressure in an incremental manner to a final pressure of 27.6 KPA (4 psia) or less and increasing the temperature of the reaction mixture in an incremental manner to a final temperature not in excess of 275 C while agitating the reaction mixture and removing the water generated by esterification of the propoxylated glycerin with the fatty acid from the reaction zone as an overhead stream, wherein the pressure and temperature are adjusted so as to avoid distillative removal of components of the reaction mixture other than water from the reaction zone, for a time effective to accomplish at least 90% esterification of the propoxylated glycerin.

The appropriate components and process aspects of each of the foregoing may be selected for the present disclosure in embodiments thereof.

SUMMARY

Disclosed in embodiments herein is a compound of the formula

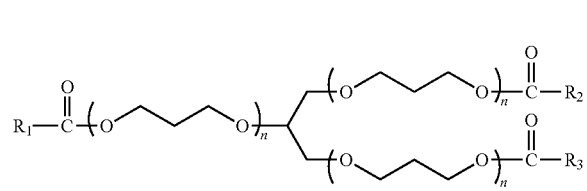

wherein $R_1$, $R_2$ and $R_3$, each, independently of the other, is (a) an alkyl group, including linear and branched, and wherein hetero atoms may or may not be present in the alkyl group, cyclic and acyclic, and substituted and unsubstituted alkyl groups, (b) an aryl group, including substituted and unsubstituted aryl groups, and wherein hetero atoms may or may not be present in the aryl group, (c) an arylalkyl group, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl portion or the alkyl portion of the arylalkyl group, or (d) an alkylaryl group, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl portion or the alkyl portion of the alkylaryl group, and wherein n is an integer.

Further disclosed in embodiments herein is a phase change ink composition including an ink carrier comprising a low viscosity functionalized wax comprising a tri-ester, wherein in embodiments the tri-ester is of the formula

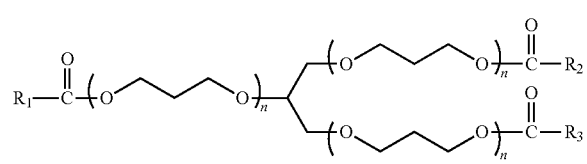

wherein $R_1$, $R_2$ and $R_3$, each, independently of the other, is an alkyl group, an aryl group, an arylalkyl group, or an alkylaryl group, and n is an integer.

Further disclosed is a method for forming an ink carrier comprising combining a glycerol propoxylate of the formula

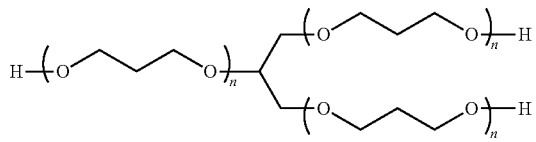

and a carboxylic acid of the formula

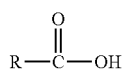

to form a low viscosity tri-ester of the formula

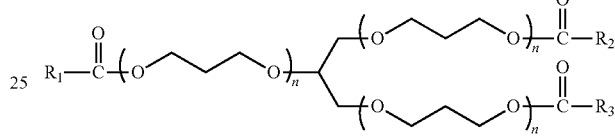

combining the low viscosity tri-ester with optional suitable components such as, for example low viscosity amides, alcohols and esters, to form an ink carrier.

Further disclosed is a method for forming a phase change ink comprising combining an ink carrier as described herein and a colorant to form a phase change ink.

Also disclosed is a method comprising incorporating into an ink jet printing apparatus a phase change ink composition comprising a colorant and an ink carrier comprising a low viscosity functionalized wax as described herein; melting the low energy phase change ink composition; and causing droplets of the melted ink to be ejected in an imagewise pattern onto a substrate.

Phase change inks disclosed herein can, in some embodiments, provide advantages including but not limited to providing phase change inks which can be formulated with less expensive pigment colorant in place of more expensive dyes. This is achieved by including components which are compatible with pigment based colorants. The present ink carriers provide in embodiments a more polar ink vehicle with functionalities that are able to interact with pigments. The present functionalized ink vehicles can, in some embodiments, also provide improved adhesion to paper. Generally, functionalized waxes have high viscosities and cannot be used as the main vehicle in an ink jet printing machine. The present phase change ink compositions provide low viscosity functionalized waxes that can be successfully employed in ink jet printing machines. In embodiments, the low viscosity of these materials is due to the star shaped structure. Further provided are phase change ink compositions employing renewable resources thereby providing simple to use, low cost, smart, and environmentally friendly ink jet components derived from renewable resources and synthesized using environmentally friendly processes. In embodiments, low viscosity tri-esters are prepared with glycerol propoxylate made from glycerol which is a byproduct of biodiesel manufacture.

DETAILED DESCRIPTION

The present disclosure is directed to a tri-ester of the formula described herein, an ink carrier comprising a low viscosity functionalized wax comprising the tri-ester, wherein, in embodiments the tri-ester is of the formula

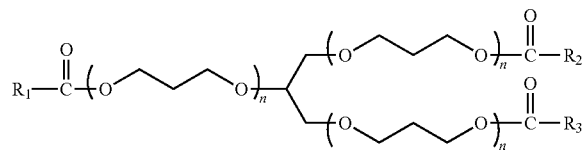

wherein $R_1$, $R_2$ and $R_3$, each, independently of the other, is an alkyl group, an aryl group, an arylalkyl group, or an alkylaryl group, and n is an integer, in embodiments, n is an integer from 1 to 50, or from 4 to 20. Phase change inks herein can comprise the above-described ink carrier and a colorant. Colorants can comprise any suitable colorant including pigmented colorants and dye based colorants.

In embodiments, $R_1$, $R_2$ and $R_3$, each, independently of the other, is (i) an alkyl group (including linear and branched, cyclic and acyclic, and substituted and unsubstituted alkyl groups, and wherein hetero atoms, such as oxygen, nitrogen, sulfur, silicon, phosphorus, boron, and the like, either may or may not be present in the alkyl group), in one embodiment with at least about 20 carbon atoms, in another embodiment with at least about 30 carbon atoms, and in yet another embodiment with at least about 50 carbon atoms, and in one embodiment with no more than about 100 carbon atoms, in another embodiment with no more than about 80 carbon atoms, and in yet another embodiment with no more than about 60 carbon atoms, and in another embodiment with at least about 25 carbon atoms, although the number of carbon atoms can be outside of these ranges;

(ii) an aryl group including substituted and unsubstituted aryl groups, wherein hetero atoms, such as oxygen, nitrogen, sulfur, silicon, phosphorus, boron, and the like, either may or may not be present in the aryl group), in one embodiment with at least about 6 carbon atoms, in another embodiment with at least about 12 carbon atoms, and in another embodiment no more than about 18 carbon atoms, although the number of carbon atoms can be outside of these ranges, (iii) an arylalkyl group (that is, where $R_1$, $R_2$ or $R_3$ is an aryl group with alkyl substituents) (including substituted and unsubstituted arylalkyl groups, wherein the alkyl portion of the arylalkyl group can be linear or branched, cyclic or acyclic, and substituted or unsubstituted, and wherein hetero atoms, such as oxygen, nitrogen, sulfur, silicon, phosphorus, boron, and the like, either may or may not be present in either the aryl or the alkyl portion of the arylalkyl group), in one embodiment with at least about 7 carbon atoms, in another embodiment with at least about 20 carbon atoms, and in another embodiment with no more than about 100 carbon atoms, although the number of carbon atoms can be outside of these ranges, or (iv) an alkylaryl group (that is where $R_1$, $R_2$ or $R_3$ is an alkyl group with an aryl substituent) (including substituted and unsubstituted alkylaryl groups, wherein the alkyl portion of the alkylaryl group can be linear or branched, cyclic or acyclic, and substituted or unsubstituted, and wherein hetero atoms, such as oxygen, nitrogen, sulfur, silicon, phosphorus, boron, and the like, either may or may not be present in either the aryl or the alkyl portion of the alkylaryl group), in one embodiment with at least about 7 carbon atoms, in another embodiment with at least about 20 carbon atoms, in another embodiment with no more than about 100 carbon atoms, although the number of carbon atoms can be outside of these ranges, wherein if substituted, the substituents on the substituted alkyl, arylalkyl, and alkylaryl groups can be (but are not limited to) halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring.

In one embodiment, at least one of $R_1$, $R_2$, and $R_3$ is an alkyl group having at least about 25 carbon atoms; and n is an integer of from about 1 to about 50.

In a specific embodiment, $R_1$, $R_2$ and $R_3$ are the same as each other. In another specific embodiment, $R_1$, $R_2$ and $R_3$ are each the same and the tri-ester is of formula

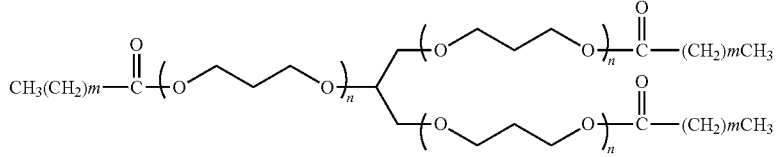

wherein m is 21 and n has an average value of 5.

In another embodiment, m is an integer having an average value of from about 15 to about 50 and n is an integer having an average value of from about 5 to about 17.

In another specific embodiment, m is 21 and n has an average value of 17. In a specific embodiment, the carboxylic acid moiety of the tri-ester is behenic acid.

In yet another specific embodiment, m has an average value of 21 and a range of from about 15 to about 30 and n has an average value of 5.

In yet another specific embodiment, m has an average value of 21 and a range of from about 15 to about 30 and n has an average value of 17. In a specific embodiment, the carboxylic acid portion of the tri-ester selected is Unicid® 350, a C22 carboxylic acid available from Baker-Petrolite Corporation. It is noted that m is smaller than the total number of carbon atoms by 1 because there is a $CH_3$ at the end of each chain.

In yet another specific embodiment m has an average value of 27 and a range of from about 20 carbon atoms to about 40 carbon atoms and n has an average value of 5.

In yet another specific embodiment m has an average value of 27 and a range of from about 20 carbon atoms to about 40 carbons atoms and n has an average value of 17. In a specific embodiment, the carboxylic acid selected is Unicid® 425, a C27 carboxylic acid available from Baker-Petrolite Corporation.

In still another specific example m has an average value of 36 with a range of from about 34 carbon atoms to about 40 carbon atoms and n has an average value of 5.

In a specific embodiment, the carboxylic acid is Isocarb® 32 (Sasol Germany GmbH), a saturated primary carboxylic acid with defined branching of the carbon chain.

In yet another specific example m has an average value of 36 with a range of from about 34 carbon atoms to about 40 carbon atoms and n has an average value of 17. In a specific embodiment, the carboxylic acid selected is Unicid® 550, a C37 carboxylic acid available from Baker-Petrolite Corporation.

In another specific example m has an average value of 47 with a range of from about 34 to about 50 and n has an average value of 5.

In another specific example m has an average value of 47 with a range of from about 34 to about 50 and n has an average value of 17. In a specific embodiment, the carboxylic acid selected is Unicid® 700, a C48 carboxylic acid available from Baker-Petrolite Corporation.

Low viscosity tri-esters herein can be prepared by any desired or suitable method. In embodiments, tri-esters herein can be prepared by reacting about one molecule of an acid of formula

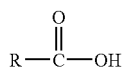

wherein R is an alkyl group, an aryl group, an arylalkyl group, or an alkylaryl group as defined for $R_1$, $R_2$ and $R_3$, above;

and about one molecule of a glycerol propoxylate of formula

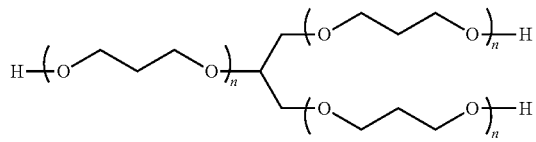

wherein n is an integer, in embodiments n is an integer from about 1 to about 50, or from about 4 to about 20;

in the presence of a tin catalyst of formula

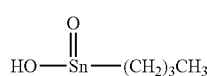

under neat conditions (i.e. in the absence of solvent) at elevated temperatures while removing water from the reaction mixture to give the tri-ester as illustrated below

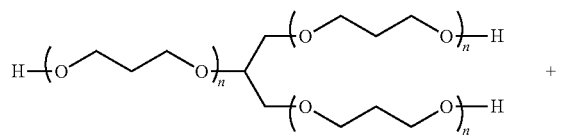

-continued

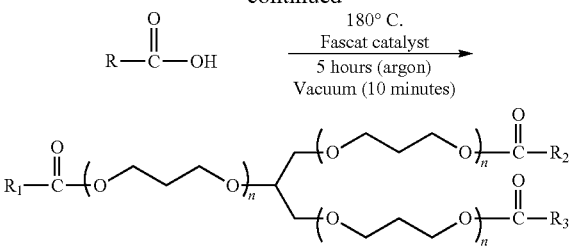

Advantageously, the reaction can be run neat, making it an environmentally friendly and cost effective process.

Glycerol propoxylates can include, for example, those having molecular weights of from about 150 to about 2000, or from about 200 to about 1500, or from about 266 to about 100.

The glycerol propoxylate and carboxylic acid are added to a reaction vessel under inert atmosphere. The reaction mixture is heated, for example to a temperature of about 100 to about 120° C., until the components melt, such as a time period of from about 0.25 to about 0.4 hours, with stirring. The temperature is then raised and the mixture stirred for about 4 to about 10 hours. Vacuum is then applied to drive off water. The product is then cooled, such as to about 25° C. to provide an off white solid. Optionally, the product can be purified by recrystallization in a suitable solvent. Suitable solvents include, but are not limited to ethanol, toluene, methanol, propanol or mixtures thereof.

In embodiments, glycerol propoxylates used herein are derived from renewable resources. In embodiments, the glycerol propoxylate is made from glycerol which is a significant by-product from biodiesel manufacture. Biodiesel is a non-petroleum diesel fuel consisting of short chain alkyl (methyl or ethyl) esters. The typical method of making biodiesel is by transesterification comprising mixing vegetable oil, alcohol, and sodium hydroxide. Glycerol is produced as a by-product in an amount of about ten percent by weight. By virtue of being a significant by-product from biodiesel manufacture, glycerol is becoming an important renewal feedstock.

In embodiments, the low viscosity functionalized tri-esters herein have a viscosity of from about 3 to less than about 100 centipoise at a temperature of about 120° C., or from about 3 centipoise to about 50 centipoise, or from about 5 centipoise to about 40 centipoise, or from about 6 centipoise to about 30 centipoise, or less than about 100 centipoises, at a temperature of about 120° C.

In embodiments, the tri-ester has an onset of crystallization of from about 66° C. to about 120° C., or greater than about 70° C., or from about 70° C. to about 105° C. or no more than about 110° C.

In embodiments, the tri-ester has an upper end melting point (that is, the point at which essentially all of the components are in liquid form) of less than about 130° C. or less than about 120° C. or less than about 100° C. In embodiments, the tri-ester has a peak of melting (that is, when melting is about half way completed) of about 50° C. or about 60° C.

Phase change ink compositions herein can be prepared by any suitable or desired method, for example, by combining an ink carrier and a colorant to form a phase change ink; wherein the ink carrier comprises a low viscosity functionalized wax comprises a tri-ester described herein.

The low viscosity functionalized wax is present in the ink in any desired or effective amount, in embodiments, the low viscosity functionalized wax comprises the majority of the ink composition, in one embodiment of at least about 30 percent by weight of the ink, in another embodiment of at least about 40 percent by weight of the ink, and in yet another embodiment of at least about 50 percent by weight of the ink, and in one embodiment equal to or less than about 80 percent by weight of the ink, in another embodiment equal to or less than about 70 percent by weight of the ink, and in yet another embodiment equal to or less than about 60 percent by weight of the ink, although the amount can be outside of these ranges.

Any other suitable ink vehicle can be included in the ink vehicle. Suitable components can include paraffins, microcrystalline waxes, polyethylene waxes, ester waxes, amides, fatty acids and other waxy materials, fatty amide containing materials, sulfonamide materials, resinous materials made from different natural sources (tall oil rosins and rosin esters, for example), and many synthetic resins, oligomers, polymers, and copolymers such as further discussed below.

Examples of suitable amides include, for example, diamides, triamides, tetra-amides, cyclic amides and the like. Suitable triamides include, for example, those disclosed in U.S. Pat. No. 6,860,930, the entire disclosure of which is incorporated herein by reference. Suitable other amides, such as fatty amides including monoamides, tetra-amides, and mixtures thereof, are disclosed in, for example, U.S. Pat. Nos. 4,889,560, 4,889,761, 5,194,638, 4,830,671, 6,174,937, 5,372,852, 5,597,856, and 6,174,937, and British Patent No. GB 2 238 792, the entire disclosures of each are incorporated herein by reference.

Other suitable carrier materials that can be used in the solid ink compositions include, for example, isocyanate-derived resins and waxes, such as urethane isocyanate-derived materials, urea isocyanate-derived materials, urethane/urea isocyanate-derived materials, mixtures thereof, and the like. Further information on isocyanate-derived carrier materials is disclosed in, for example, U.S. Pat. Nos. 5,750,604, 5,780,528, 5,782,966, 5,783,658, 5,827,918, 5,830,942, 5,919,839, 6,255,432, and 6,309,453, British Patents Nos. GB 2 294 939, GB 2 305 928, GB 2 305 670, and GB 2 290 793, and PCT Publications WO 94/14902, WO 97/12003, WO 97/13816, WO 96/14364, WO 97/33943, and WO 95/04760, the entire disclosures of each of which are incorporated herein by reference.

Further examples of suitable ink carrier materials include, for example, ethylene/propylene copolymers, such as those available from Baker Petrolite. Commercial examples of such copolymers include, for example, Petrolite CP-7 (Mn=650), Petrolite CP-11 (Mn=1,100, Petrolite CP-12 (Mn=1,200) and the like. The copolymers may have, for example, a melting point of from about 70° C. to about 150° C., such as from about 80° C. to about 130° C. or from about 90° C. to about 120° C. and a molecular weight range (Mn) of from about 500 to about 4,000.

Another type of ink carrier material may be n-paraffinic, branched paraffinic, and/or naphthenic hydrocarbons, typically with from about 5 to about 100, such as from about 20 to about 80 or from about 30 to about 60 carbon atoms, generally prepared by the refinement of naturally occurring hydrocarbons, such as BE SQUARE 185 and BE SQUARE 195, with molecular weights (Mn) of from about 100 to about 5,000, such as from about 250 to about 1,000 or from about 500 to about 800, for example such as available from Baker Petrolite.

Highly branched hydrocarbons, typically prepared by olefin polymerization, such as the VYBAR materials available from Baker Petrolite, including VYBAR™ 253 (Mn=520), VYBAR™ 5013 (Mn=420), and the like, may also be used. In addition, the ink vehicle may be an ethoxylated alcohol, such as available from Baker Petrolite and of the general formula

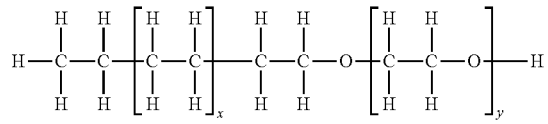

wherein x is an integer of from about 1 to about 50, such as from about 5 to about 40 or from about 11 to about 24 and y is an integer of from about 1 to about 70, such as from about 1 to about 50 or from about 1 to about 40. The materials may have a melting point of from about 60° C. to about 150° C., such as from about 70° C. to about 120° C. or from about 80° C. to about 110° C. and a molecular weight (Mn) range of from about 100 to about 5,000, such as from about 500 to about 3,000 or from about 500 to about 2,500. Commercial examples include UNITHOX® 420 (Mn=560), UNITHOX® 450 (Mn=900), UNITHOX® 480 (Mn=2,250), UNITHOX® 520 (Mn=700), UNITHOX® 550 (Mn=1,100), UNITHOX® 720 (Mn=875), UNITHOX® 750 (Mn=1,400), and the like.

As an additional example, the ink vehicle may be made of fatty amides, such as monoamides, tetra-amides, mixtures thereof, and the like, for example such as described in U.S. Pat. No. 6,858,070, which is hereby incorporated herein by reference in its entirety. Suitable monoamides may have a melting point of at least about 50° C., for example from about 50° C. to about 150° C., although the melting point can be outside these ranges. Specific examples of suitable monoamides include, for example, primary monoamides and secondary monoamides. Stearamide, such as KEMAMIDE® S available from Witco Chemical Company and CRODAMIDE® S available from Croda, behenamide/arachidamide, such as KEMAMIDE® B available from Witco and CRODAMIDE® BR available from Croda, oleamide, such as KEMAMIDE® U available from Witco and CRODAMIDE® OR available from Croda, technical grade oleamide, such as KEMAMIDE® O available from Witco, CRODAMIDE® O available from Croda, and UNISLIP® 1753 available from Uniqema, and erucamide such as KEMAMIDE® E available from Witco and CRODAMIDE® ER available from Croda, are some examples of suitable primary amides. Behenyl behenamide, such as KEMAMIDE® EX666 available from Witco, stearyl stearamide, such as KEMAMIDE® S-180 and KEMAMIDE® EX-672 available from Witco, stearyl erucamide, such as KEMAMIDE® E-180 available from Witco and CRODAMIDE® 212 available from Croda, erucyl erucamide, such as KEMAMIDE® E-221 available from Witco, oleyl palmitamide, such as KEMAMIDE® P-181 available from Witco and CRODAMIDE® 203 available from Croda, and erucyl stearamide, such as KEMAMIDE® S-221 available from Witco, are some examples of suitable secondary amides. Additional suitable amide materials include KEMAMIDE® W40 (N,N'-ethylenebisstearamide), KEMAMIDE® P181 (oleyl palmitamide), KEMAMIDE® W45 (N,N'-thylenebisstearamide), and KEMAMIDE® W20 (N,N'-ethylenebisoleamide).

Further optional components can include high molecular weight linear alcohols, such as those available from Baker Petrolite and of the general formula

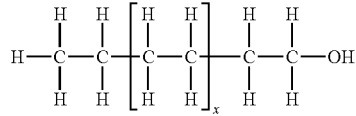

wherein x is an integer of from about 1 to about 50, such as from about 5 to about 35 or from about 11 to about 23, may also be used as the ink vehicle. These materials may have a melting point of from about 50° C. to about 150° C., such as from about 70° C. to about 120° C. or from about 75° C. to about 110° C., and a molecular weight (Mn) range of from about 100 to about 5,000, such as from about 200 to about 2,500 or from about 300 to about 1,500. Commercial examples include the UNILIN® materials such as UNILIN® 425 (Mn=460), UNILIN® 550 (Mn=550), UNILIN® 700 (Mn=700), and distilled alcohols, the viscosity of which at the jetting temperature in one embodiment can be from about 5 to about 50% higher than the non-distilled alcohol.

Further examples include hydrocarbon-based waxes, such as the homopolymers of polyethylene available from Baker Petrolite and of the general formula

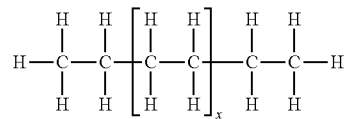

wherein x is an integer of from about 1 to about 200, such as from about 5 to about 150 or from about 12 to about 105. These materials may have a melting point of from about 60° C. to about 150° C., such as from about 70° C. to about 140° C. or from about 80° C. to about 130° C. and a molecular weight (Mn) of from about 100 to about 5,000, such as from about 200 to about 4,000 or from about 400 to about 3,000. Example waxes include PW400 (Mn about 400), distilled PW400, in one embodiment having a viscosity of about 10% to about 100% higher than the viscosity of the undistilled POLYWAX® 400 at about 110° C., POLYWAX 500 (Mn about 500), distilled POLYWAX® 500, in one embodiment having a viscosity of about 10% to about 100% higher than the viscosity of the undistilled POLYWAX® 500 at about 110° C., POLYWAX 655 (Mn about 655), distilled POLYWAX® 655, in one embodiment having a viscosity of about 10% to about 50% lower than the viscosity of the undistilled POLYWAX® 655 at about 110° C., and in yet another embodiment having a viscosity of about 10% to about 50% higher than the viscosity of the undistilled POLYWAX® 655 at about 110° C. POLYWAX 850 (Mn about 850), POLYWAX 1000 (Mn about 1,000), and the like.

Further examples include modified maleic anhydride hydrocarbon adducts of polyolefins prepared by graft copolymerization, such as those available from Baker Petrolite and of the general formulas

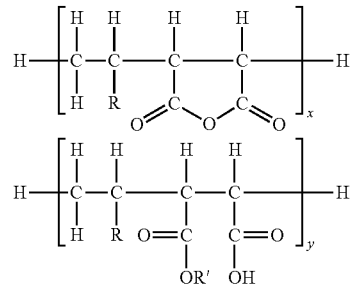

wherein R is an alkyl group with from about 1 to about 50, such as from about 5 to about 35 or from about 6 to about 28 carbon atoms, R' is an ethyl group, a propyl group, an isopropyl group, a butyl group, an isobutyl group, or an alkyl group with from about 5 to about 500, such as from about 10 to about 300 or from about 20 to about 200 carbon atoms, x is an integer of from about 9 to about 13, and y is an integer of from about 1 to about 50, such as from about 5 to about 25 or from about 9 to about 13, and having melting points of from about 50° C. to about 150° C., such as from about 60° C. to about 120° C. or from about 70° C. to about 100° C.; and those available from Baker Petrolite and of the general formula

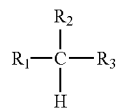

wherein $R_1$ and $R_3$ are hydrocarbon groups and $R_2$ is either of one of the general formulas

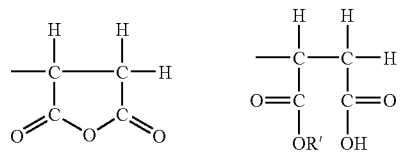

or a mixture thereof, wherein R' is an isopropyl group, which materials may have melting points of from about 70° C. to about 150° C., such as from about 80° C. to about 130° C. or from about 90° C. to about 125° C., with examples of modified maleic anhydride copolymers including CERAMER® 67 (Mn=655, Mw/Mn=1.1), CERAMER® 1608 (Mn=700, Mw/Mn=1.7), and the like.

Additional examples of suitable ink vehicles for the phase change inks include rosin esters; polyamides; dimer acid amides; fatty acid amides, including ARAMID® C; epoxy resins, such as EPOTUF® 37001, available from Riechold Chemical Company; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides, including KETJENFLEX® MH and KETJENFLEX® MS80; benzoate esters, such as BENZOFLEX® S552, available from Velsicol Chemical Company; phthalate plasticizers; citrate plasticizers; maleate plasticizers; sulfones, such as diphenyl sulfone, n-decyl sulfone, n-amyl sulfone, chlorophenyl methyl sulfone; polyvinyl pyrrolidinone copolymers; polyvinyl pyrrolidone/polyvinyl acetate copolymers; novolac resins, such as DUREZ® 12 686, available from Occidental Chemical Company; and natural product waxes, such as beeswax, monton wax, candelilla wax, GILSONITE® (American Gilsonite Company), and the like; mixtures of linear primary alcohols with linear long chain amides or fatty acid amides, such as those with from about 6 to about 24 carbon atoms, including PARICIN® 9 (propylene glycol monohydroxystearate), PARICIN® 13 (glycerol monohydroxystearate), PARICIN® 15 (ethylene glycol monohydroxystearate), PARICIN® 220 (N(2-hydroxyethyl)-12-hydroxystearamide), PARICIN® 285 (N,N'-ethylene-bis-12-hydroxystearamide), FLEXRICIN® 185 (N,N'-ethylene-bis-ricinoleamide), and the like. Further, linear long chain sulfones with from about 4 to about 16 carbon atoms, such as n-propyl sulfone, n-pentyl sulfone, n-hexyl sulfone, n-heptyl sulfone, n-octyl sulfone, n-nonyl sulfone, n-decyl sulfone, n-undecyl sulfone, n-dodecyl sulfone, n-tridecyl sulfone, n-tetradecyl sulfone, n-pentadecyl sulfone, n-hexadecyl sulfone, and the like, are suitable ink vehicle materials.

In addition, the ink vehicles described in U.S. Pat. No. 6,906,118, which is incorporated herein by reference in its entirety, may also be used. The ink vehicle may contain a branched triamide such as those described in U.S. Pat. No. 6,860,930, the disclosure of which is also incorporated by reference herein in its entirety,

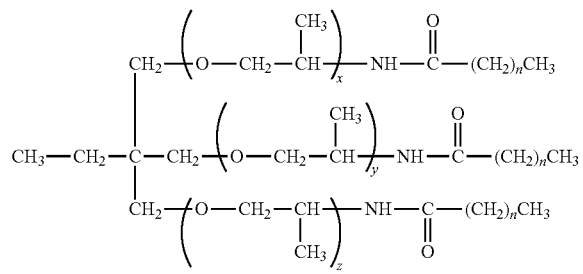

wherein n has an average value of from about 34 equal to or less than 40, where x, y and z can each be zero or an integer, and wherein the sum of x, y, and z is from about 5 and equal to or less than 6.

A plasticizer, which can be either a solid or liquid plasticizer, such as benzyl phthalates, triaryl phosphate esters, pentaerythritol tetrabenzoate, dialkyl adipate, dialkyl phthalates, dialkyl sebacate, alkyl benzyl phthalates, ethylene glycol monostearate, glycerol monostearate, propylene glycol monostearate, dicyclohexyl phthalate, diphenyl isophthalate, triphenyl phosphate, dimethyl isophthalate, and mixtures thereof, or the like can also be included in the ink carrier. The plasticizer is present in the ink carrier in any desired or effective amount, in one embodiment of at least about 0.05% by weight of the ink carrier, in another embodiment of at least about 1% by weight of the ink carrier, and in yet another embodiment of at least about 2% by weight of the ink carrier, and in one embodiment of equal to or less than about 15% by weight of the ink carrier, in another embodiment of equal to or less than about 10% by weight of the ink carrier, and in yet another embodiment of equal to or less than about 5% by weight of the ink carrier, although the amount can be outside of these ranges. Examples of suitable plasticizers include SANTICIZER® 278, SANTICIZER® 154, SANTICIZER®160, SANTICIZER® 261 (commercially available from Monsanto), and the like or mixtures thereof.

A hindered amine antioxidant can be present in the ink in any desired or effective amount, in one embodiment of at least about 0.001 percent by weight of the ink carrier, in another embodiment of at least about 0.05 percent by weight of the ink carrier, and in yet another embodiment of at least about 0.10 percent by weight of the ink carrier, and in one embodiment of equal to or less than about 0.50 percent by weight of the ink carrier, in another embodiment of equal to or less than about 0.25 percent by weight of the ink carrier, and in yet another embodiment of equal to or less than about 0.15 percent by weight of the ink carrier, although the amount can be outside of these ranges.

Examples of suitable hindered amine antioxidants include those of general formula

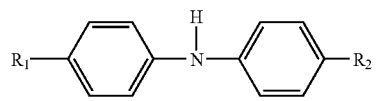

wherein $R_1$ and $R_2$ each, independently of the other, can be a hydrogen atom or an alkyl group, including linear, branched, saturated, unsaturated, cyclic, substituted, and unsubstituted alkyl groups, and wherein hetero atoms, such as oxygen, nitrogen, sulfur, silicon, phosphorus, boron, either may or may not be present in the alkyl group, in one embodiment with at least 1 carbon atom, if substituted, substitutions can be alkyl or phenyl.

Specific examples of suitable hindered amine antioxidants include the following antioxidants commercially available from Crompton; NAUGUARD® 445 where $R_1=R_2=C(CH_3)_2Ph$, NAUGUARD® 635 where $R_1=R_2=-CH(CH_3)Ph$, NAUGUARD® PS-30 where $R_1=C_4$ or $C_8$, $R_2=C_4$ or $C_8$ and the like.

A hindered phenol antioxidant can also be provided. In one embodiment the hindered phenol is present in a relatively high concentration. A high concentration of hindered phenol antioxidant maximizes long term thermal stability by delaying the onset of the oxidation itself. The hindered phenol antioxidant is present in the ink in any desired or effective amount, in one embodiment of at least about 0.01% by weight of the ink carrier, in another embodiment of at least about 0.5% by weight of the ink carrier, and in yet another embodiment of at least about 1.5% by weight of the ink carrier, and in one embodiment equal to or less than about 4.0% by weight of the ink carrier, in another embodiment equal to or less than about 3.0% by weight of the ink carrier, and in yet another embodiment equal to or less than about 2.5% by weight of the ink carrier, although the amount can be outside of these ranges. Specific examples of suitable hindered phenol antioxidants include ETHANOX® 330, ETHANOX® 310, ETHANOX® 314, ETHANOX® 376 (commercially available from Albemarle) and the like. Also commercially available from Ciba Specialty Chemicals are IRGANOX® 1010, IRGANOX® 1035, IRGANOX®1076, IRGANOX® 1330 and the like. Mixtures of two or more of these hindered phenol antioxidants can also be employed.

A dispersant can be present in the ink in any desired or effective amount for purposes of dispersing and stabilizing the pigment or alternative particles present in the ink vehicle. The dispersant is present in any desired or effective amount, in one embodiment of at least about $1\times10^{-5}$% by weight of the ink carrier, in another embodiment of at least about $1\times10^{-3}$% by weight of the ink carrier, and in yet another embodiment of at least about $5\times10^{-1}$% by weight of the ink carrier, and in one embodiment equal to or less than about 30% by weight of the ink carrier, in another embodiment equal to or less than about 20% by weight of the ink carrier, and in yet another embodiment equal to or less than about 10% by weight of the ink carrier, although the amount can be outside of these ranges. Specific examples of suitable dispersants are polyester dispersants such as those disclosed in U.S. Pat. No. 6,702,884, U.S. Pat. No. 6,841,590, the disclosures of which are totally incorporated herein by reference. Dispersants can include but are not limited to Solsperse® 16000, Solsperse® 28000, Solsperse® 32500, Solsperse® 38500, Solsperse® 39000, Solsperse® 54000, Solsperse® 17000, Solsperse® 17940 from Noveon, Inc. as well as mixtures thereof. Examples of suitable polyester dispersants are disclosed in U.S. Pat. No. 3,996,059 the disclosure of which is totally incorporated herein by reference. Where the dispersant is a polyester of the formula

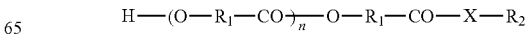

wherein each $R_1$ is an alkylene group, including linear, branched, saturated, unsaturated, cyclic, substituted, and unsubstituted alkyl groups containing at least 8 carbon atoms, such as from about 8 to about 40 carbon atoms or from about 8 to about 30 or from about 8 to about 20 carbon atoms, although the numbers can be outside these ranges, if substituted, substitutions can be (but are not limited to) halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, and the like, wherein two or more substituents can be joined together to form a ring;

X is (i) an oxygen atom, (ii) an alkylene group which is attached to the carbonyl group through an oxygen or nitrogen atom with at least 2 carbon atoms; $R_2$ is (i) a hydrogen atom, (ii) a primary, secondary or tertiary amine group or a salt thereof with an acid, or a quaternary ammonium salt group; and n is an integer representing a number of repeating groups, for example from 2 to about 20 or from about 2 to about 10.

Other dispersants may include but are not limited to Solsperse® 13240, Solsperse® 13940 from Noveon, Inc., as well as mixtures thereof.

Another class of suitable dispersants include urethane derivatives of oxidized synthetic or petroleum waxes, such as those available from Baker Petrolite and of the general formulas

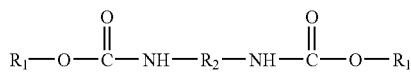

wherein $R_1$ is an alkyl group of the formula $CH_3(CH_2)_n$, n is an integer of from about 5 to about 200, for example from about 10 to about 150 or from about 10 to about 100 and $R_2$ is an arylene group, may also be used as the ink vehicle. These materials may have a melting point of from about 60° C. to about 120° C., such as from about 70° C. to about 100° C. or from about 70° C. to about 90° C. Commercial examples of such materials include, for example, Baker Petrolite CA-11 (Mn=790, Mw/Mn=2.2), Petrolite WB-5 (Mn=650, Mw/Mn=1.7), Petrolite WB-17 (Mn=730, Mw/Mn=1.8), and the like.

Other examples of suitable dispersants are polyalkylene succinimide dispersants such as those disclosed in U.S. Pat. No. 6,858,070, the disclosure of which is totally incorporated herein by reference. Dispersants can include the Chevron Oronite OLOA® 11000, OLOA® 11001, OLOA® 11002, OLOA® 11005, OLOA® 371, OLOA® 375, OLOA® 411, OLOA® 4500, OLOA® 4600, OLOA® 8800, OLOA® 8900, OLOA® 9000, OLOA® 9200 and the like, commercially available from Chevron Oronite Company LLC, Houston, Tex., as well as mixtures thereof. Examples of suitable polyalkylene succinimides and their precursors and methods of making them are disclosed in, for example, U.S. Pat. No. 3,172,892, U.S. Pat. No. 3,202,678, U.S. Pat. No. 3,280,034, U.S. Pat. No. 3,442,808, U.S. Pat. No. 3,361,673, U.S. Pat. No. 3,172,892, U.S. Pat. No. 3,912,764, U.S. Pat. No. 5,286,799, U.S. Pat. No. 5,319,030, U.S. Pat. No. 3,219,666, U.S. Pat. No. 3,381,022, U.S. Pat. No. 4,234,435, and European Patent Publication 0 776 963, the disclosures of each of which are totally incorporated herein by reference.

A rosin ester resin, mixtures thereof, or the like can also be included in the ink carrier. The rosin ester resin is present in the ink carrier in any desired or effective amount, in one embodiment of at least about 0.5% by weight of the ink carrier, in another embodiment of at least about 2% by weight of the ink carrier, and in yet another embodiment of at least about 3% by weight of the ink carrier, and in one embodiment of equal to or less than about 20% by weight of the ink carrier, in another embodiment equal to or less than about 15% by weight of the ink carrier, and in yet another embodiment equal to or less than about 10% by weight of the ink carrier, although the amount can be outside of these ranges. Examples of suitable rosin ester resins include PINECRYSTAL® KE-100 (commercially available from Arakawa), and the like.

The ink carrier can be present in the phase change ink prepared in any desired or effective amount, in one embodiment in an amount of at least about 50% by weight of the ink, in another embodiment of at least about 70% by weight of the ink, and in yet another embodiment of at least about 90% by weight of the ink, and in one embodiment equal to or less than about 99% by weight of the ink, in another embodiment equal to or less than about 98% by weight of the ink, and in yet another embodiment equal to or less than about 95% by weight of the ink, although the amount can be outside of these ranges.

In one specific embodiment, the ink carrier has a melting point of less than about 110° C., and in another embodiment of less than about 100° C., although the melting point of the ink carrier can be outside of these ranges.

The phase change ink compositions can also contain a colorant. Any desired or effective colorant can be employed, including dyes, pigments, mixtures thereof, and the like, provided that the colorant can be dissolved or dispersed in the ink vehicle. The phase change carrier compositions can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Ciba-Geigy); Direct Brilliant Pink B (Crompton & Knowles); Aizen Spilon Red C-BH (Hodogaya Chemical); Kayanol Red 3BL (Nippon Kayaku); Levanol Brilliant Red 3BW (Mobay Chemical); Levaderm Lemon Yellow (Mobay Chemical); Spirit Fast Yellow 3G; Aizen Spilon Yellow C-GNH (Hodogaya Chemical); Sirius Supra Yellow GD 167; Cartasol Brilliant Yellow 4GF (Sandoz); Pergasol Yellow CGP (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc. A (Morton-Thiokol); Diaazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF), Neozapon Black X51 [C.I. Solvent Black, C.I. 12195] (BASF), Sudan Blue 670 [C.I. 61554] (BASF), Sudan Yellow 146 [C.I. 12700] (BASF), Sudan Red 462 [C.I. 26050] (BASF), Intratherm Yellow 346 commercially available from Crompton and Knowles, C.I. Disperse Yellow 238, Neptune Red Base NB543 (BASF, C.I. Solvent Red 49), Neopen Blue FF-4012 commercially available from BASF, Lampronol Black BR commercially available from ICI (C.I. Solvent Black 35), Morton Morplas Magenta 36 (C.I. Solvent Red 172), metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are totally incorporated herein by reference, and commercially available from, for example, Milliken & Company as Milliken Ink Yellow 12, Milliken Ink Blue 92, Milliken Ink Red 357, Milliken Ink Yellow 1800, Milliken Ink Black 8915-67, uncut Reactant Orange X-38, uncut Reactant Blue X-17, Solvent Yellow 162, Acid Red 52, Solvent Blue 44, and uncut Reactant Violet X-80.

In a specific embodiment, the phase change ink carrier herein comprises a low viscosity functionalized wax that provides a more polar ink vehicle that is compatible with pigments. In embodiments, the present ink carriers enable replacement of expensive dyes with less expensive pigment colorants.

Examples of suitable pigments include Violet Toner VT-8015 (commercially available from Paul Uhlich); Paliogen Violet 5100 (commercially available from BASF); Paliogen Violet 5890 (commercially available from BASF); Permanent Violet VT 2645 (commercially available from Paul Uhlich); Heliogen Green L8730 (commercially available from BASF); Argyle Green XP-111-S (commercially available from Paul Uhlich); Brilliant Green Toner GR 0991 (commercially available from Paul Uhlich); Lithol Scarlet D3700 (commercially available from BASF); Toluidine Red (commercially available from Aldrich); Scarlet for Thermoplast NSD PS PA (commercially available from Ugine Kuhlmann of Canada); E.D. Toluidine Red (commercially available from Aldrich); Lithol Rubine Toner (commercially available from Paul Uhlich); Lithol Scarlet 4440 (commercially available from BASF); Bon Red C (commercially available from Dominion Color Company); Royal Brilliant Red RD-8192 (commercially available from Paul Uhlich); Oracet Pink RF (commercially available from Ciba-Geigy); Paliogen Red 3871K (commercially available from BASF); Paliogen Red 3340 (commercially available from BASF); Lithol Fast Scarlet L4300 (commercially available from BASF); Heliogen Blue L6900, L7020 (commercially available from BASF); Heliogen Blue K6902, K6910 (commercially available from BASF); Heliogen Blue D6840, D7080 (commercially available from BASF); Sudan Blue OS (commercially available from BASF); Neopen Blue FF4012 (commercially available from BASF); PV Fast Blue B2G01 (commercially available from American Hoechst); Irgalite Blue BCA (commercially available from Ciba-Geigy); Paliogen Blue 6470 (commercially available from BASF); Sudan III (commercially available from Red Orange) (commercially available from Matheson, Colemen Bell); Sudan II (commercially available from Orange) (commercially available from Matheson, Colemen Bell); Sudan Orange G (commercially available from Aldrich), Sudan Orange 220 (commercially available from BASF); Paliogen Orange 3040 (commercially available from BASF); Ortho Orange OR 2673 (commercially available from Paul Uhlich); Paliogen Yellow 152, 1560 (commercially available from BASF); Lithol Fast Yellow 0991K (commercially available from BASF); Paliotol Yellow 1840 (commercially available from BASF); Novoperm Yellow FGL (commercially available from Hoechst); Permanent Yellow YE 0305 (commercially available from Paul Uhlich); Lumogen Yellow D0790 (commercially available from BASF); Suco-Yellow L1250 (commercially available from BASF); Suco-Yellow D1355 (commercially available from BASF); Suco Fast Yellow D1355, D1351 (commercially available from BASF); Hostaperm Pink E (commercially available from American Hoechst); Fanal Pink D4830 (commercially available from BASF); Cinquasia Magenta (commercially available from Du Pont); Paliogen Black L0084 (commercially available from BASF); Pigment Black K801 (commercially available from BASF); and carbon blacks such as Regal 330° (commercially available from Cabot), Carbon Black 5250, Carbon Black 5750 (commercially available from Columbia Chemical), and the like.

Also suitable are the colorants disclosed in U.S. Pat. No. 6,472,523, U.S. Pat. No. 6,726,755, U.S. Pat. No. 6,476,219, U.S. Pat. No. 6,576,747, U.S. Pat. No. 6,713,614, U.S. Pat. No. 6,663,703, U.S. Pat. No. 6,755,902, U.S. Pat. No. 6,590,082, U.S. Pat. No. 6,696,552, U.S. Pat. No. 6,576,748, U.S. Pat. No. 6,646,111, U.S. Pat. No. 6,673,139, U.S. Pat. No. 6,958,406, and U.S. Pat. No. 7,053,227, the disclosures of each of which are totally incorporated herein by reference.

The colorant is present in the phase change ink in any desired or effective amount to obtain the desired color or hue, in one embodiment at least about 0.1 percent by weight of the ink composition, and in another embodiment at least about 0.2 percent by weight of the ink composition, and in one embodiment no more than about 15 percent by weight of the ink composition, and in another embodiment no more than about 8 percent by weight of the ink composition, although the amount can be outside of these ranges.

The ink compositions disclosed herein in one embodiment have melting points in one embodiment equal to or less than about 130° C., in another embodiment equal to or less than about 120° C., in a further embodiment equal to or less than about 110° C., and in still another embodiment equal to or less than about 100° C., although the melting point can be outside of these ranges.

The ink compositions prepared by the process disclosed herein generally have melt viscosities, at the jetting temperature which can be equal to or less than about 145° C., in one embodiment equal to or less than about 130° C., and in another embodiment equal to or less than about 120° C., in a further embodiment equal to or less than about 110° C., and in yet another embodiment equal to or less than about 80° C., although the jetting temperature can be outside of these ranges, which are in one embodiment equal to or less than about 30 cps, in another embodiment equal to or less than about 25 cps, and in yet a further embodiment equal to or less than about 20 cps, and in another embodiment no less than about 2 cps, in a further embodiment no less than about 3 cps, and in yet a further embodiment no less than about 4 cps, although the melt viscosity can be outside of these ranges.

The inks disclosed herein can be employed in apparatus for direct printing ink jet processes and in indirect (offset) printing ink jet applications. Another embodiment is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. The inks prepared as disclosed herein can be employed in apparatus for indirect (offset) printing ink jet applications. Another embodiment is directed to a process which comprises incorporating an ink prepared as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements.

Any suitable substrate or recording sheet can be employed, including plain papers such as XEROX® 4024 papers, XEROX® Image Series papers, Courtland 4024 DP paper, ruled notebook paper, bond paper, silica coated papers such as Sharp Company silica coated paper, JuJo paper, Hammermill Laserprint Paper, and the like, transparency materials, fabrics, textile products, plastics, polymeric films, inorganic substrates such as metals and wood, and the like.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Examples 1-9

Preparation of Tri-Esters

A series of tri-esters, Examples 1-9 as shown in Table 1, were synthesized using the following representative procedure. Glycerol propoxylate (10.14 wt %, 35.47 grams; Molecular number (Mn) ~266, from Sigma-Aldrich Fine Chemicals, Milwaukee, Wis.), Unicid® 550 (89.86 wt %, 314.35 grams, a carboxylic acid available from Baker Petrolite, Sugar Land, Tex.) and Fascat® 4100 (0.1 wt %, 0.35 grams, a butylstannoic acid catalyst available from Arkema, Inc., Philadelphia, Pa.) were added to a 1 Liter reaction kettle with a 4N lid and equipped with mechanical stirrer, thermocouple and Dean Stark trap, under inert atmosphere. The reaction mixture was heated to 100° C., during which all the components melted, began stirring, and the temperature was raised to 180° C. The mixture was stirred at 180° C. for 5 hours during which some water was collected. Vacuum was applied for 10 minutes to drive off all the water, the vacuum was stopped, replaced with inert atmosphere and heating was stopped. The product was cooled to 120° C., poured in Aluminum trays and cooled to room temperature to give an off white solid. Fourier Transform Infrared spectroscopy (FT-IR) was used to evaluate the product. FT-IR showed a peak at 1738 cm-1 indicating the presence of an ester. Complex viscosity was measured on a Rheometrics Fluid Spectrometer RFS3 in a cone-plate geometry (50 millimeters) using a low to high shear rate at 120° C. and is reported in Table 1.

The series of tri-esters shown in Table 1 were synthesized using the procedure as described hereinabove. These are higher molecular weight functionalized waxes with relatively low viscosity. Commercially available functionalized waxes like Clariant's acid waxes (e.g. Licowax) have lower molecular weight (C22-28) and relatively higher viscosity (14 centipoise (cps) at 120° C.). Montan acid waxes have viscosities around 30 cps at 100° C. Due to the low viscosities, these tri-esters can be used as the main component in the present solid inks.

Tri-esters of Examples 2, 3, 4 and 7 are hard materials and are less brittle than the distilled polyethylene wax 500.

TABLE 1

| | | | | | | | | |
|---|---|---|---|---|---|---|---|---|
| | | | Low Viscosity Tri-Esters | | | | | |
| Tri-ester | Glycerol | Carboxylic | | | DSC Results (° C.) | | | |
| Example | Propoxylate | Acid | | Viscosity at | Onset of | Peak of | Peak of | End of |
| Number | Mn | Wt % | R | Wt % | 120° C. (cps) | Crystallization | Crystallization | Melting | Melting |
| 1 | 266 | 15 | Unicid® 350 (~C22) | 85 | 7.83 | 77.42 | 50.25 | 60.16 | 92.78 |
| 2 | 266 | 12.82 | Unicid® 425 (~C28) | 87.18 | 11.86 | 85.78 | 72.55 | 80.5 | 105.57 |
| 3 | 266 | 10.14 | Unicid® 550 (~C37) | 89.86 | 17.16 | 93.76 | 90.77 | 85.55 | 106.38 |
| 4 | 266 | 7.9 | Unicid® 700 (~C48) | 93.1 | 23.26 | 98.41 | 91.93 | 97.57 | 112.22 |
| 5 | 266 | 14.91 | Isocarb® 32 (branched C32 acid) | 85.09 | 5.83 | — | — | — | — |
| 6 | 1000 | 40 | Unicid® 350 | 60 | 8.24 | — | — | — | — |
| 7 | 1000 | 24.4 | Unicid® 700 | 75.6 | 21.77 | 99.57 | 90.97 | 97.12 | 114.93 |
| 8 | 1000 | 31.95 | Unicid® 425 | 68.05 | 11.7 | 92.57 | 78.06 | 72.89 | 101.44 |
| 9 | 266 | 20.6 | Behenic acid (C22 acid) | 79.4 | 6.7 | — | — | — | — |

Examples 10-14

Preparation of Ink Compositions

The ink compositions of Table 2 were prepared in 2 aliquots of 150 milliliter glass beakers by adding the respective amount of the component in parts by weight as herein described for ink Example 2. 55.58 wt %, 27.79 grams of the tri-ester of Example 2, 22.43 wt %, 11.21 grams of behenyl behenate (Kester Wax, obtained from Koster Keunen, Watertown, Conn.), 9.75 wt %, 4.88 grams of stearyl stearamide, S-180 available from Chemtura Corporation), 9.75 wt %, 4.88 grams of triamide resin prepared as described U.S. Pat. No. 6,860,930, for Example, as in Example II of U.S. Pat. No. 6,860,930, which is hereby incorporated by reference herein in its entirety. The materials were melted together at a temperature of about 120° C. in an oven for about 1 hour and transferred to a reaction block (from H+P Labortechnik GmbH, München) controlled with a Telemodel 40CT which was set at 120° C. The mixture was stirred for about 2 hours at about 300 rpm. To this mixture was then added 2.5 wt %, 1.25 grams of Solvent Red 49 (BASF). The ink was stirred for an additional 3 hours and then filtered through a 0.45 μm Parker® disc filter at 120° C. with an applied pressure of 6 psig. The filtered phase change ink was poured in an aluminum mold and allowed to solidify to form an ink stick. The inks were characterized by measuring rheology on a Rheometrics Fluid Spectrometer RFS3 in a cone-plate geometry (50 millimeters).

TABLE 2

Ink Compositions

| Component | Ink Example 1 wt % | Ink Example 2 wt % | Ink Example 3 wt % | Ink Example 4* wt % | Ink Example 5* wt % |
|---|---|---|---|---|---|
| Tri-ester of Example 1 | 97.50 | — | — | — | — |
| Tri-ester of Example 2 | — | 55.58 | 51.00 | 82.35 | — |
| Tri-ester of Example 3 | — | — | — | — | 72.35 |
| Behenyl behenate (Kester Wax) | — | 22.43 | 27.00 | — | — |
| High MW Linear Alcohol (Unilin® 425) | — | — | — | 15 | 25 |
| Stearyl Stearamide | — | 9.75 | 9.75 | — | — |
| Triamide resin[1] | — | 9.75 | 9.75 | — | — |
| Naugard® 445 | — | — | — | 0.15 | 0.15 |
| Solvent Red 49 (BASF) | 2.50 | 2.50 | 2.50 | 2.50 | 2.50 |
| Total | 100 | 100.01 | 100 | 100 | 100 |
| Viscosity (cps) at 120° C. (filtered) | 10.34 | 10.58 | 9.70 | | |

*Ink examples 4 and 5 are prophetic examples.
[1]triamide resin prepared as described in U.S. Pat. No. 6,860,930, incorporated by reference hereinabove.

The inks of Examples 1, 2, and 3 were jetted directly to paper using a XEROX® PHASER® 860 Sold Ink Printer and glossed and folded. Printing results are shown in Table 3.

TABLE 3

| | PHASER® 860 Magenta Ink (Direct to Paper) | Ink Example 3 |
|---|---|---|
| Jetting Temperature | 112° C. | 125° C. |
| 60° C. Gloss | 22.5 | 19.5 |
| Fold (crease) | 0.38% | 0.37% |

Ink Example 3 had gloss and crease comparable to that of XEROX® PHASER® 860 magenta ink printed directly to paper.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. An ink carrier comprising:
a tri-ester of the formula

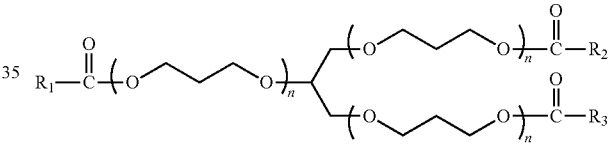

wherein $R_1$, $R_2$ and $R_3$, each, independently of the other, is (a) an alkyl group, including linear and branched, and wherein hetero atoms may or may not be present in the alkyl group, cyclic and acyclic, and substituted and unsubstituted alkyl groups, (b) an aryl group, including substituted and unsubstituted aryl groups, and wherein hetero atoms may or may not be present in the aryl group, (c) an arylalkyl group, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl portion or the alkyl portion of the arylalkyl group, or (d) an alkylaryl group, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl portion or the alkyl portion of the alkylaryl group, and wherein n is an integer.

2. The ink carrier of claim 1, wherein at least one of $R_1$, $R_2$, and $R_3$ is an alkyl group having from about 20 to about 100 carbon atoms.

3. The ink carrier of claim 1, wherein at least one of $R_1$, $R_2$, and $R_3$ is an alkyl group having about 25 carbon atoms.

4. The ink carrier of claim 1, wherein $R_1$, $R_2$, and $R_3$ are the same as each other.

5. The ink carrier of claim 1, wherein n is an integer of from about 1 to about 50.

6. The ink carrier of claim 1, wherein the tri-ester is of the formula

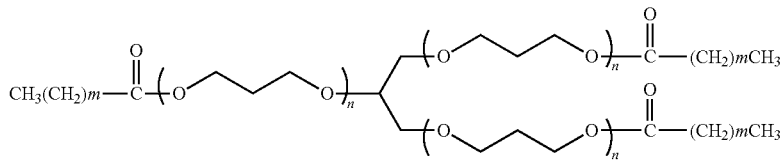

wherein m is an integer having an average value of from about 15 to about 50 and n is an integer having an average value of from about 5 to about 17.

7. The ink carrier of claim 1, wherein the tri-ester has a viscosity of from about 3 to less than about 100 centipoise at a temperature of about 120° C.

8. The ink carrier of claim 1, wherein the tri-ester has an onset of crystallization of greater than about 70° C. to about 105° C.

9. The ink carrier of claim 1, wherein the tri-ester has a peak of melting at about 60° C. and an upper end melting point of less than about 120° C.

10. The ink carrier of claim 1, wherein the tri-ester comprises at least one component derived from a renewable resource.

11. A phase change ink comprising a colorant and an ink carrier, wherein the ink carrier comprises a tri-ester of the formula

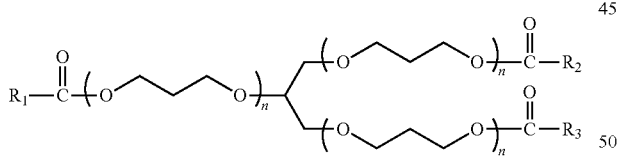

wherein $R_1$, $R_2$ and $R_3$, each, independently of the other, is (a) an alkyl group, including linear and branched, and wherein hetero atoms may or may not be present in the alkyl group, cyclic and acyclic, and substituted and unsubstituted alkyl groups, (b) an aryl group, including substituted and unsubstituted aryl groups, and wherein hetero atoms may or may not be present in the aryl group, (c) an arylalkyl group, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl portion or the alkyl portion of the arylalkyl group, or (d) an alkylaryl group, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl portion or the alkyl portion of the alkylaryl group, and wherein n is an integer from about 1 to about 50.

12. The phase change ink of claim 11, wherein at least one of $R_1$, $R_2$, and $R_3$ is an alkyl group having from about 20 to about 100 carbon atoms.

13. The phase change ink of claim 11, wherein $R_1$, $R_2$, and $R_3$ are the same as each other.

14. The phase change ink of claim 11, wherein the tri-ester is of the formula

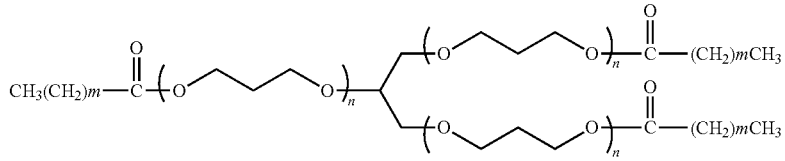

wherein m is an integer having an average value of from about 15 to about 50 and n is an integer having an average value of from about 5 to about 17.

15. The phase change ink of claim 11, wherein the tri-ester comprises at least one component derived from a renewable resource.

16. The phase change ink of claim 11, wherein the tri-ester is prepared with a glycerol propoxylate starting material that is a by-product of biodiesel manufacture via transesterification of vegetable oil.

17. The phase change ink of claim 11, wherein the colorant is a pigment.

18. The phase change ink of claim 11, wherein the colorant is a dye.

19. A method which comprises:
incorporating into an ink jet printing apparatus a phase change ink composition comprising a colorant and an ink carrier comprising a low a tri-ester of the formula

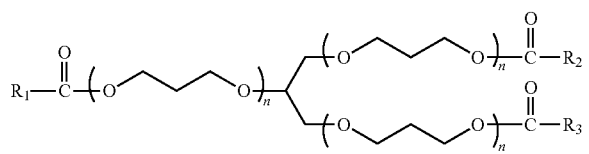

wherein $R_1$, $R_2$ and $R_3$, each, independently of the other, is (a) an alkyl group, including linear and branched, and wherein hetero atoms may or may not be present in the alkyl group, cyclic and acyclic, and substituted and unsubstituted alkyl groups, (b) an aryl group, including substituted and unsubstituted aryl groups, and wherein hetero atoms may or may not be present in the aryl group, (c) an arylalkyl group, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl portion or the alkyl portion of the arylalkyl group, or (d) an alkylaryl group, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl portion or the alkyl portion of the alkylaryl group, and wherein n is an integer from about 1 to about 50;

wherein the tri-ester is prepared with at least one component derived from a renewable resource.

melting the low energy phase change ink composition; and causing droplets of the melted ink to be ejected in an imagewise pattern onto a substrate.

20. A compound of the formula

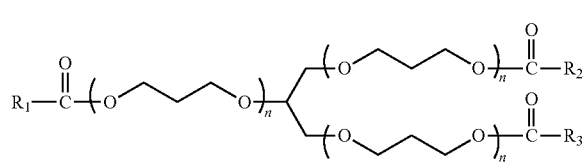

wherein $R_1$, $R_2$ and $R_3$, each, independently of the other, is (a) an alkyl group, including linear and branched, and wherein hetero atoms may or may not be present in the alkyl group, cyclic and acyclic, and substituted and unsubstituted alkyl groups, (b) an aryl group, including substituted and unsubstituted aryl groups, and wherein hetero atoms may or may not be present in the aryl group, (c) an arylalkyl group, including substituted and unsubstituted arylalkyl groups, wherein the alkyl portion of the arylalkyl group can be linear or branched, cyclic or acyclic, and substituted or unsubstituted, and wherein hetero atoms either may or may not be present in either the aryl portion or the alkyl portion of the arylalkyl group, or (d) an alkylaryl group, including substituted and unsubstituted alkylaryl groups, wherein the alkyl portion of the alkylaryl group can be linear or branched, cyclic or acyclic, and substituted or unsubstituted, and wherein hetero atoms either may or may not be present in either the aryl portion or the alkyl portion of the alkylaryl group, and wherein n is an integer.

21. The compound of claim 20, wherein at least one of $R_1$, $R_2$, and $R_3$ is an alkyl group having at least about 25 carbon atoms; and wherein n is an integer of from about 1 to about 50.

22. The compound of claim 20, wherein $R_1$, $R_2$, and $R_3$ are the same as each other.

23. The compound of claim 20, wherein the tri-ester is of the formula

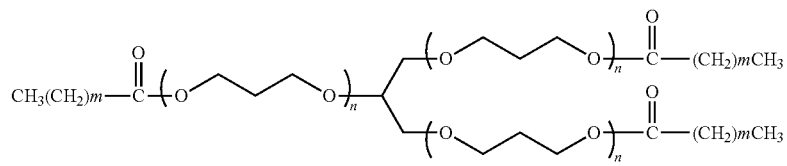

wherein m is an integer having an average value of from about 15 to about 50 and n is an integer having an average value of from about 5 to about 17.

24. The compound of claim 20, wherein the tri-ester has a viscosity of from about 3 to less than about 100 centipoise at a temperature of about 120° C.

25. The compound of claim 20, wherein the portion of the tri-ester corresponding to a glycerol propoxylate is derived from a renewable resource.

* * * * *